United States Patent
Gillette et al.

(10) Patent No.: US 7,323,091 B1
(45) Date of Patent: Jan. 29, 2008

(54) MULTIMODE ELECTROCHEMICAL SENSING ARRAY

(75) Inventors: Timothy C. Gillette, Brookline, MA (US); Steven J. West, Hull, MA (US)

(73) Assignee: Orion Research, Inc., Beverly, MA (US)

( * ) Notice: Subject to any disclaimer, the term of this patent is extended or adjusted under 35 U.S.C. 154(b) by 601 days.

(21) Appl. No.: 10/669,454

(22) Filed: Sep. 24, 2003

Related U.S. Application Data

(60) Provisional application No. 60/413,054, filed on Sep. 24, 2002.

(51) Int. Cl.
*G01N 27/414* (2006.01)

(52) U.S. Cl. .................. 204/416; 204/412; 257/253

(58) Field of Classification Search ............. 204/412, 204/461, 417, 418, 416; 257/253
See application file for complete search history.

(56) References Cited

U.S. PATENT DOCUMENTS

| | | | | | |
|---|---|---|---|---|---|
| 4,839,000 | A | * | 6/1989 | Eddowes | .................. 205/778 |
| 5,427,871 | A | * | 6/1995 | Garshol et al. | ............. 429/119 |
| 5,833,824 | A | * | 11/1998 | Benton | ...................... 204/416 |
| 6,236,075 | B1 | * | 5/2001 | Hsiung et al. | ............... 257/252 |
| 6,280,586 | B1 | * | 8/2001 | Wolf et al. | ................ 257/253 |
| 6,280,587 | B1 | * | 8/2001 | Matsumoto | ............ 204/403.01 |

OTHER PUBLICATIONS wiseGeek article entitled "What is a Varistor?" downloaded from www.wisegeek.com on Aug. 22, 2007.*

* cited by examiner

*Primary Examiner*—Alex Noguerola
(74) *Attorney, Agent, or Firm*—Cesari and McKenna, LLP

(57) ABSTRACT

A multimode electrochemical sensing array formed on an integrated circuit chip is structured to provide electrochemical determination of acidity or alkalinity, as well as electrochemical and potentiometric measurement of oxidation/reduction potentials, conductivity measurements, electrostatic discharge protection, and ground provisioning.

11 Claims, 4 Drawing Sheets

MULTIMODE ELECTROCHEMICAL SENSING ARRAY

This application claims the priority of U.S. Provisional Patent Application No. 60/413,054, filed Sep. 24, 2002.

BACKGROUND OF THE INVENTION

1. Field of the Invention

The invention relates to electrochemistry and, more particularly, to electrochemical sensors.

2. Background Information

Electrochemical sensors are used in an expansive variety of applications to measure parameters of importance to chemical and physical processes of all kinds, from biochemical to industrial. A variety of electrochemical measurements are of frequent interest. For example, many chemical processes, including biochemical processes, optimally occur at a particular pH; monitoring the pH of a solution involved in the process thus frequently provides important information as to the process and can signal departures from normal. Another type of measurement that is frequently made is the conductivity of a solution. Conductivity measurements provide information as to the ionic strength of the solution, and are often important in their own right as well as in providing information as to the effect of conductivity on chemical reactions. In addition to these basic characteristics, measurements of characteristics such as the oxidation/reduction potential of a reaction occurring at specific electrodes provide information as to the nature of the constituents taking part in reactions.

Typically, electrochemical sensors are specialized for the particular parameter being measured. Thus, pH is usually determined by means of a potentiometric sensor that commonly includes a glass membrane that is selective for the $H^+$ ion. Acidity or alkalinity is usually determined by a titration, i.e., by adding aliquots of a base in the case of an acid solution, and of an acid in the case of a basic solution, until the preexisting acid or base in the solution is entirely neutralized. A sensor, which may be a pH sensor, is used to determine the point at which balance is achieved. Conductance of a solution is typically determined by yet another instrument, which applies a voltage across a measured length of the solution and which measures the resultant current. Thus, to make several types of measurements on a particular solution typically requires the use of several different instruments.

Semiconductor chips have heretofore been used as sensor elements in electrochemical sensors. One such element is a Field Effect Transistor, specifically, an Ion-Selective Field Effect Transistor (ISFET). In such a device, the transistor is formed with the usual gate, source, and drain electrodes, with the potential applied to the gate controlling the conductivity between the source and the drain. In contrast to conventional FET devices, however, the gate electrode is left exposed and thus can be placed directly in contact with a liquid solution when the chip is immersed in such a solution. The gate is thus made responsive to the electrochemical potential of the solution in its neighborhood, and the current flow between the transistor source and drain provides an indication of this potential.

A device of the type described above has been known for use as an electrochemical sensor in an aqueous solution. See van der Schoot and Bergveld, *Sensor and Actuators*, vol. 8 (1985), pp. 11-22. In this application, a "generating electrode" in the form of a thin layer of a noble metal such as gold or platinum is deposited around the exposed gate of the ISFET. A counter electrode and a reference electrode are likewise deposited on the chip substrate, in the vicinity of the generating electrode. The electrodes are of substantial area. Current pulses applied between the generating electrode and the counter electrode generate titrant for the solution in which the sensor is immersed. If the current is made anodic at the generating electrode, $H^+$ ions are generated at the location of the gate, and these ions titrate a basic solution. Conversely, if the current is made cathodic at the generating electrode, $OH^-$ ions are generated at the location of the gate, and these ions titrate an acidic solution. In either case, the end point is detected by the change in pH at the ISFET gate.

SUMMARY OF THE INVENTION

In accordance with the present invention, I provide a multimode electrochemical sensing array formed entirely on an integrated circuit chip and operable to provide a multiplicity of different electrochemical measurements. Specifically, the chip is capable of providing for measurement of the pH of a solution and its conductivity. Further, it is structured to measure both the acidity and the alkalinity of a solution by local titration, as well as to measure oxidation/reduction potentials of reactions taking place at one or more electrodes.

The present invention extends the capabilities of ISFET electrochemical sensors to encompass not only electrochemical determination of acidity or alkalinity, but also electrochemical and potentiometric measurement of oxidation/reduction potentials, conductivity measurements, electrostatic discharge protection, and ground provisioning.

In particular, the array of the present invention comprises a substrate chip on which is formed, in addition to an ISFET having an exposed gate, a plurality of electrodes usable both in connection with, and independent of, the ISFET to perform a plurality of functions including titrations, redox measurements, conductivity measurements, ISFET protection, and grounding. In a preferred embodiment, there are at least two electrodes of substantial size (e.g., 1¼ mm. by 2½ mm) that can serve as counter electrodes for some of the measurements to be made. The substantial area of the electrodes limits the current density at their surface, and thus prevents bubbling, with its consequent disturbance of measurements. Either of both of these electrodes, singly or in parallel, are used as counter electrode in ISFET titration measurements, as well as in measurements independent of the ISFET. Further, a corresponding pair of additional electrodes of substantially smaller size (e.g., ⅛ mm. by ⅛ mm.) is formed in a notch in the respective counter electrodes to enable measurement of conductivity. For this purpose, a current generator is applied between the large counter electrodes and the resultant voltage between the smaller electrodes is measured, the ratio of the applied current to the resultant voltage indicating the conductivity of the solution. Knowledge of the conductivity can be especially important in insuring that a given solution has sufficient conductivity to perform a particular titration, as well as in enabling conductivity-dependent corrections to be applied to the titration if necessary. The ability to make such conductivity measurements simply by quickly switching one or more of the provided electrodes into and out of the system as necessary is a distinct advantage of the present invention.

Either or both of the counter electrodes may also be used in redox titrations. In particular, a current applied to a counter electrode in the presence of oxidants or reductants will create electrolysis products which diffuse over the adjacent corresponding small electrode. The resultant change in potential is measured by the small electrode as the oxidized or reduced species diffuses over it.

One or more of the counter electrodes can also conveniently be connected to a given reference potential (e.g., "ground") to fix the potential of the solution in which it is immersed.

As taught in van der Schoot, referenced above, the gate electrode of the ISFET used in the present invention is surrounded by an electrode (for ease of reference, called the "proximal" electrode) that is used to generate titrant for ISFET-measured titrations. Like the counter electrodes, this electrode is of substantial size (in one embodiment of the invention, 2 mm. by $^{11}/_{16}$ mm.). In accordance with the present invention, this electrode is used not only as one of the current-generating electrode pairs, as in van der Schoot, but also as one of the electrodes in one or more of the non-ISFET measurements. Thus, in a counter-electrode redox titration as described above, the current source driving the oxidation/reduction reaction is connected between the electrode surrounding the ISFET gate and one of the counter electrodes. Further, in accordance with the present invention, the proximal electrode is structured to provide light-shielding for the ISFET. This is achieved by forming the distal electrode of platinum and extending it over all portions of the ISFET susceptible to light except that portion of the ISFET gate which is to sense changes in the solution pH. In a preferred embodiment of the invention, the proximal electrode was on the order of $^{11}/_{16}$ mm. wide and 2 mm. long, with a central window of $^{11}/_{16}$ mm. by $^{9}/_{16}$ mm. through which the ISFET gate was exposed. Further, the proximal electrode was spaced on the order of 0.6 mm. from the nearest counter electrode so as to insure minimal interaction between the latter and the reactions taking place at the proximal electrode during a measurement.

In acid/base titrations, a significant nonlinearity in response may be observed when plotting the time to reach end point against the acid/base concentration. We have found that the measurements may be linearized by using a ramped driving current, instead of a constant driving current, particularly for strong acids and bases.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
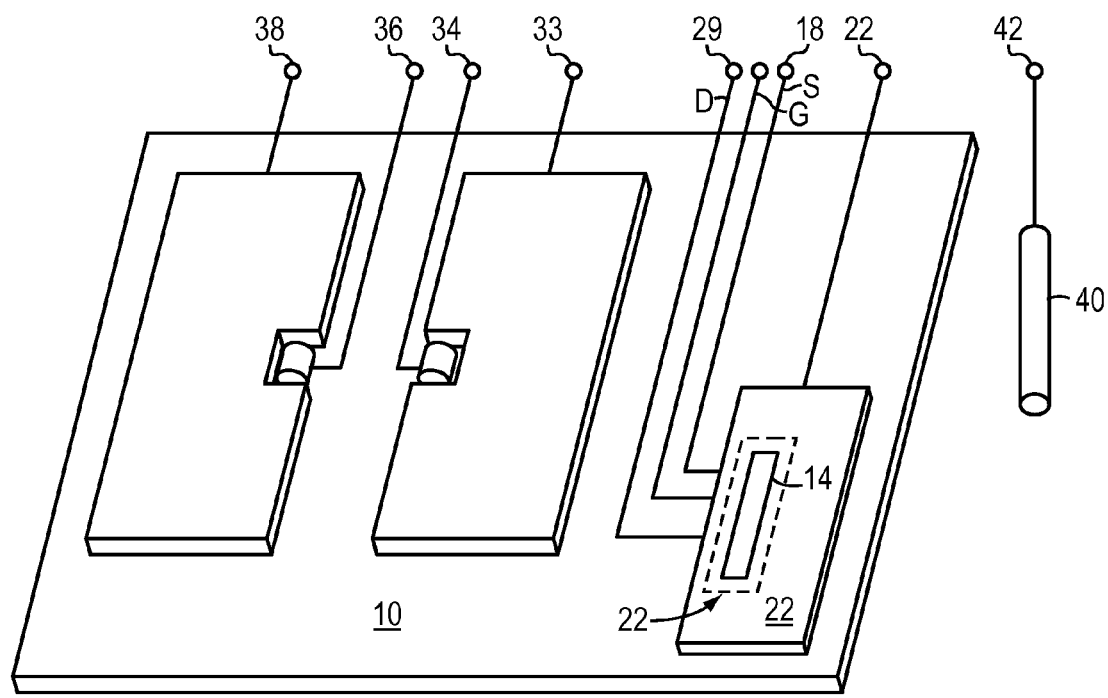
FIG. 1 is an illustrative view in perspective of a multimode sensor chip in accordance with the present invention.

In FIG. 1, a semiconductor chip 10 has an Ion Selective Field Effect Transistor (ISFET) 12 (indicated by dotted lines) formed on it in the usual manner. The surface of the chip is covered by an insulating material such as silicon dioxide or silicon nitride, but the Gate of the ISFET is left exposed through an aperture 14 in a thin layer electrode 22 of a noble metal such as platinum or gold that has been deposited on the chip to closely surround the gate area but not contact it for reasons shortly to be described. For ease of reference, the electrode 22 is referred to herein as the "proximal" electrode. A terminal 18 is connected to the Source electrode of the ISFET, and a terminal 20 to its Drain. A terminal 22' connects to electrode 22. Also on the chip, but remote from the ISFET, are a pair of large electrodes ("distal electrodes") 24, 26 partially encompassing a corresponding pair of small electrodes, 28, 30. Like the electrode 22, the electrodes 24, 26, 28 and 30 are preferably formed of a noble metal such as platinum or gold, and are deposited in thin layers on the surface of the chip. Terminals 32 and 34 connect to the electrodes 24 and 28, respectively, while terminals 36 and 38 connect to electrodes 30 and 26, respectively.

The electrodes 24 and 26 are positioned relatively remotely from the electrode 22, i.e., are positioned sufficiently far from electrode 22 that decomposition products which may be generated at electrode 22 will not have sufficient time during a measurement in question to diffuse to or from electrodes 24 and/or 26. Thus, generation of such products at one electrode will not be able to adversely affect, nor be affected by, those which may be generated at the other electrodes. In this connection, the transverse offset in the position of the electrode 22 with respect to electrodes 24, 26 will slightly lengthen the distance between the respective electrodes and thus assist in further isolating them in this respect.

The electrodes 24, 26 are also of substantial area in comparison to that of electrode 22, preferably at least as large as the latter, and desirably larger. This helps to minimize the current density at the electrodes 24, 26 for a given measurement, and thus limits bubbling which might otherwise interfere with the measurement.

An external reference electrode 40, itself well known in the art of potentiometric measurements, having terminal 42, is also used in performing the measurements of the present invention. The electrode 40 provides a fixed half-cell reference potential when used in conjunction with an ion-selective half cell as described here.

Figure 2:
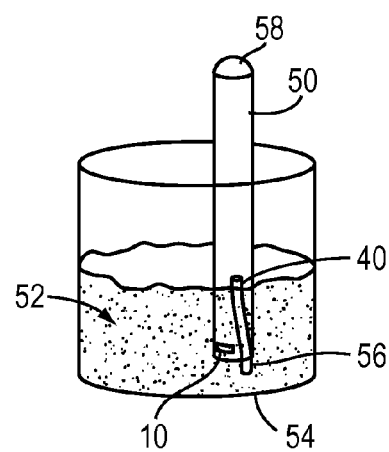
FIG. 2 is an illustrative view of a multimode sensor chip in accordance with the present invention mounted on a probe together with a reference electrode.

FIG. 2 shows a view in perspective of the measuring chip 10 mounted on a probe 50 and immersed in a test solution 52 in a beaker 54. The reference electrode 40 (indicted by dotted lines) is contained within the probe 50 and is connected to the test solution via a liquid junction (e.g., a porous plug) 56. A cable 58 carries the leads from the chip 10 and reference electrode 40 for connection to external instruments as necessary.

A first important electrochemical measurement that can be made with the array of the present invention is an electrochemical titration of a test solution. In such a measurement, a titrant (acidic or basic) is generated by driving an electrode in the immediate vicinity of a sensing electrode in a test solution with a current of sufficient strength to electrolyze the solution and provide acid or base for neutralizing corresponding amounts is of basic or acidic materials in the solution. When the titrant entirely neutralizes the test solution (the point at which this occurs being referred to as the equivalence point), the pH of the solution rapidly changes, and this change is detected by a sensor to determine the end of the titration. The acidity or alkalinity of the solution is determined as the total amount of titrant consumed. This is obtained by monitoring the current applied to the driven electrode and the time during which it is applied.

Figure 3:
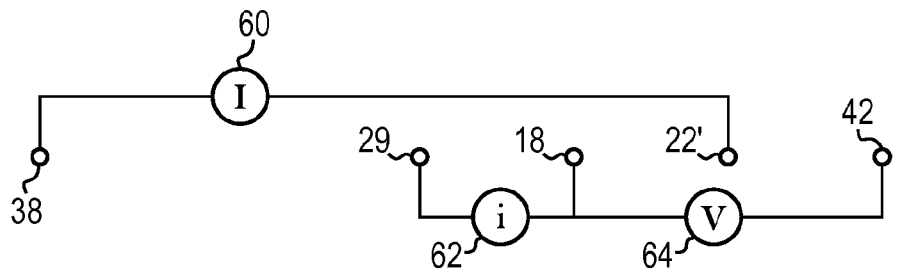
FIG. 3 is a connector diagram for utilization of the chip of the present invention in an electrochemical determination of acidity or alkalinity.

In accordance with one aspect of the present invention, at least one of the electrodes 24, 26 is used as part of a current-applying electrode pair in connection with the electrode 22. FIG. 3 shows the circuit configuration for such measurements. In FIG. 3, a current source 60 is connected between terminals 22' and 38 (and thus between electrodes 22 and 26, respectively). The current source is polarized in such manner as to provide anodic (oxidizing) or cathodic (reducing) action at electrode 22, depending on whether the solution to be titrated is basic or acidic. A current meter (i) 62 connected between the terminals 18 and 20 measures the current between the Drain and Source of the ISFET. This current is a function of the pH of the solution as sensed by the Gate. A reference potential is monitored by a voltmeter (v) 64 connected between the Source terminal 18 and the terminal 42 of reference electrode 40.

In FIG. 3 and in the following Figures, it will be understood that the circuitry is illustrated as connected for measurement with the chip 10 immersed in a test solution. Thus, the path of the various circuits is completed through the test solution. For example, the current I that flows in the external circuit through current generator 60 follows a return loop from one terminal to another through the test solution.

The electrodes 22 and 26 comprise a current-applying pair for creating the desired titrant. Since electrode 26 is remote from electrode 22, the electrolysis products at electrode 26 are not able to diffuse sufficiently quickly through the test solution to the vicinity of electrode 22 and thus cannot interfere with the potentials sensed at the FET Gate. To give an example of the speed with which titrations may be performed with the present invention, acidity determinations of 2, 10, and 20 mM hydroxyisobutyric acid solutions reached end point in less than 1, 2 And 4 seconds, respectively, using a constant current of 20 microamperes as the driving source.

Figure 4:
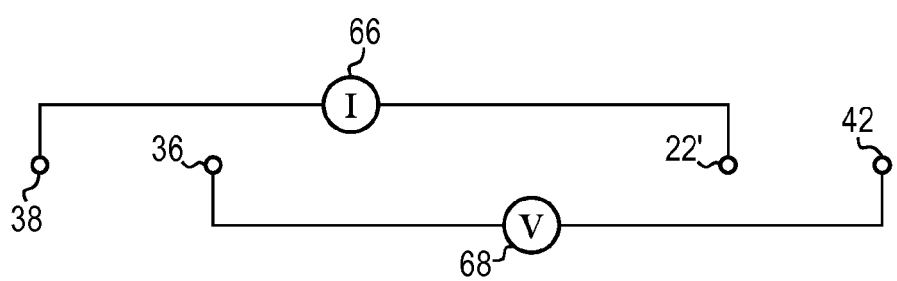
FIG. 4 is a connector diagram for utilization of the chip of the present invention in an electrochemically-determined oxidation-reduction reaction.

The electrodes 22 and 26 may also be used in a reverse configuration and independent of ISFET 12. In particular, either one or both may serve as the current-applying electrode for an oxidation-reduction reaction whose end-point is measured with respect to the reference electrode 40. Thus, in FIG. 4, a current source (I) 66 is connected between terminals 38 (leading to electrode 26) and 22' (leading to electrode 22). Additionally, a voltage meter (v) 68 is connected between terminal 36 (leading to electrode 30) and terminal 42 (leading to reference electrode 40). At the electrode 26, titrable oxidants or reductants (depending on the polarity of the current source) are produced to titrate corresponding reductants or oxidants in the solution in the vicinity of the electrode. Adjacent electrode 30, in combination with reference half cell 40, monitors the potential in the test solution at the site of electrode 40 and enables determination of the end point of the oxidation/reduction reaction.

Figure 5:
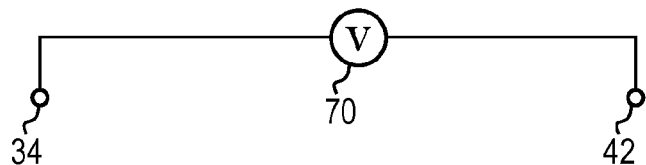
FIG. 5 is a connector diagram for utilization of the chip of the present invention in a non-electrochemical oxidation/reduction potential measurement.

Of course, the chip may be used in a simple, non-electrochemical oxidation/reduction potential measurement. In this case, the connections to the chip are configured as shown in FIG. 5, in which a voltmeter 70 is connected between terminal 34 (and thus electrode 28) and terminal 42 (and thus reference electrode 40). Of course, electrode 30 may be used for this purpose as well, either separately or in parallel with electrode 28.

Figure 6:
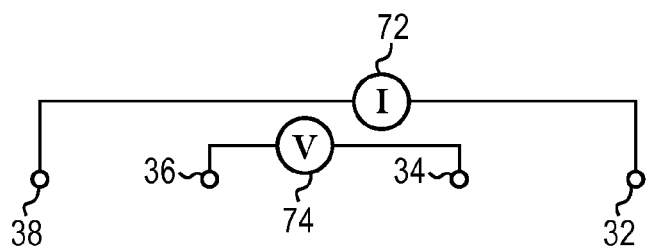
FIG. 6 is a connector diagram for utilization of the chip of the present invention in measurement of the conductivity of a test solution.

Still another measurement that is made by the chip of the present invention is that of the conductivity of a test solution. In FIG. 6, a current source (I) 72 is connected between terminal 38 (and thus electrode 26) and terminal 32 (and thus electrode 24). Additionally, a voltage meter (v) 74 is connected between terminal 36 (and thus electrode 30) and terminal 34 (and thus electrode 28). The electrodes 28 and 30 measure the potential drop occasioned by the current I flowing between terminals 24 and 26 and thus the conductance of the test solution can be determined from a ratio of the two.

Figure 7:
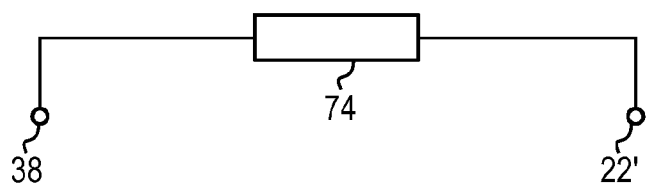
FIG. 7 is a connector diagram for utilization of the chip of the present invention in providing electrostatic discharge protection to an ISFET mounted on the chip.

Yet another benefit of the multi-mode chip of the present invention is the ability to provide an electrostatic discharge protection to the ISFET. As is known to those skilled in the art, transistors in general are subject to damage from buildup of charge on them. In the present invention, this may be forestalled by the circuit of FIG. 7 in which an is element such as a varistor 74 is connected between terminal 38 (and thus electrode 26) and terminal 22' (and thus electrode 22). When the potential on electrode 22 reaches the level at which further increase in potential might likely cause damage, varistor 74 fires, discharging the electrode 22 to a safe potential.

In some measurements, it is desirable or necessary to ground the test solution. This is readily done in the chip of the present invention by connecting one or more of the electrodes 24-30 to ground (not shown).

In the above discussion, the various aspects of the present invention have several times been illustrated with use of a single one of the large electrodes 24, 26 or smaller electrodes 28, 30. From the detailed description of the invention given above, it will be clear to those skilled in the art that frequently two or more of these electrodes can be connected to serve as a single electrode without otherwise changing the overall functionality of the particular circuit.

Figure 8A:
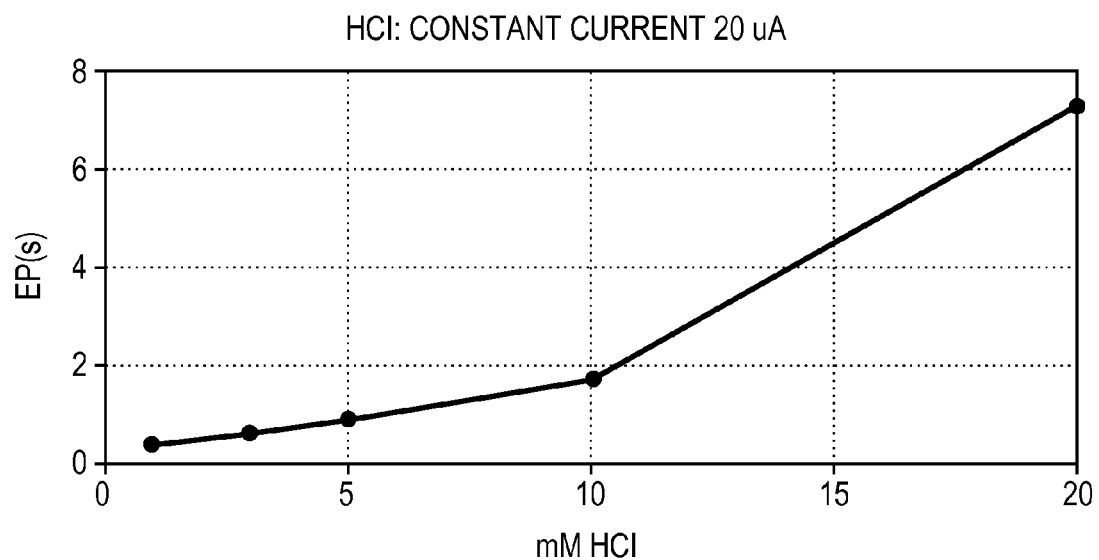
FIGS. 8A and 8B illustrates the improvement in measurement linearity achieved by using a ramped-current generator for titillating strong acids and bases.
Figure 8B:
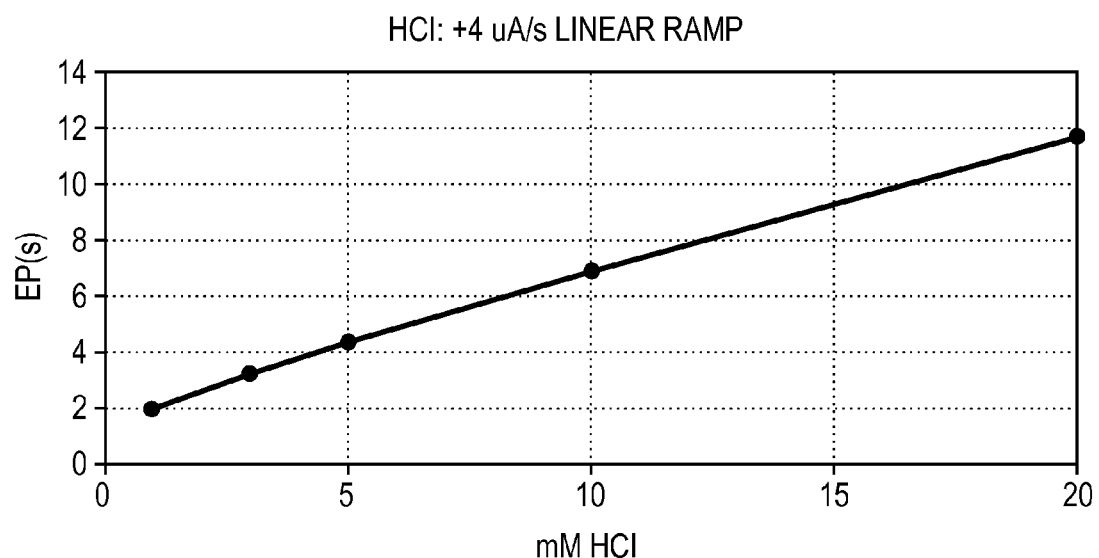

In the case of strong acid and bases, we have found it desirable to drive the active electrode (i.e., the electrode at which a reactant is produced for use in titration) with a current ramp, instead of a constant current. FIGS. 8A and 8B show the effect of such a procedure as applied to the titration of hydrochloric acid, HCl. In these figures, the abscissas show the time to reach end point in seconds (EP(s)) for several samples of different strength; the ordinates show the strength of the respective samples, in millimoles (mM).

In FIG. 8A, a constant current of 20 microamperes (20 uA) was applied. The time to reach end-point is seen to increase relatively linearly with concentration up to a concentration of about 10 mM, at which point the slope of the EP-Concentration curve breaks sharply upward.

FIG. 8B, in contrast, shows the result of increasing the driving current as the concentration increases. In this figure, the driving current was in the form of a linear ramp of slope 4 microamperes/second (4 uA/s), starting at time zero. As can be seen, the slope of the EP-Concentration curve is essentially linear over the entire range depicted.

Figure 9:
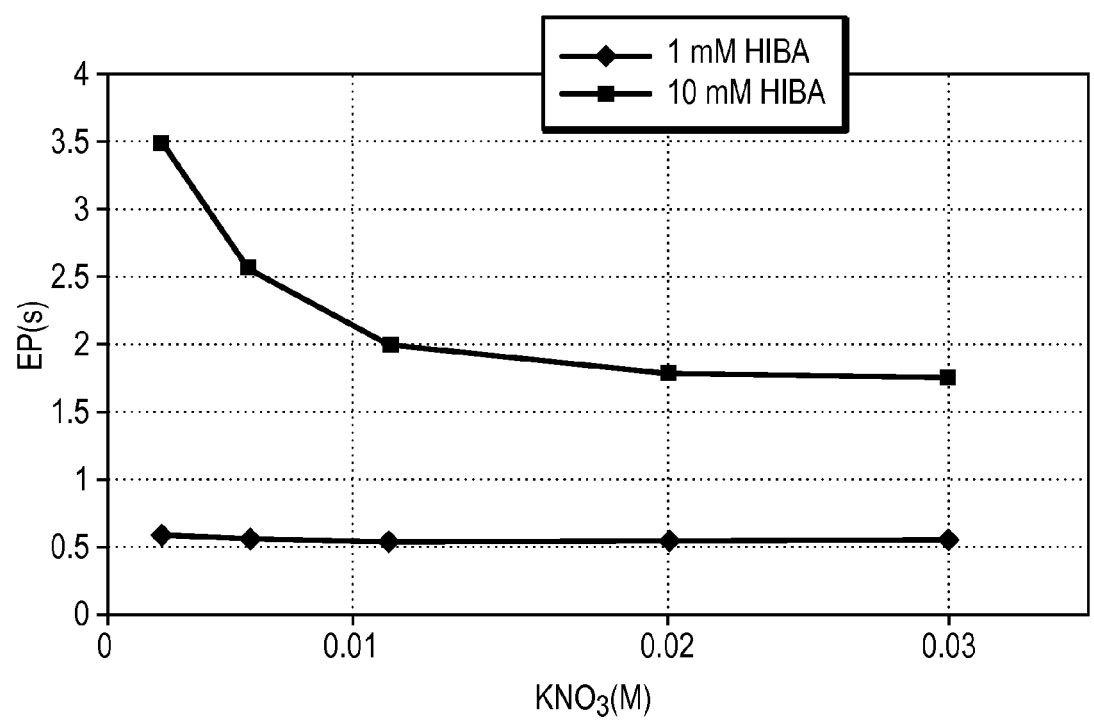
FIG. 9 illustrates the benefits achieved by providing an on-chip conductivity measuring facility in the present invention.

As noted above, the conductivity of a solution can influence the time required to reach end point in a titration, since the conductively is reflective of the rate at which ions can diffuse through the solution after their generation. As shown in FIG. 9, increasing the background electrolyte concentration, (in this case, potassium nitrate, $KNO_3$), has a significant effect on the time to reach end point for higher concentration levels (10 mM) of a substance such as hydroxyisobutyric acid, reducing this time from approximately 3.5 seconds for very low concentrations of $KNO_3$ (approximately 0.005 mM) to less than 2 seconds for higher concentrations (0.01 mM and above).

In accordance with one aspect of the present invention, therefore, before a titration is performed with the chip of the present invention, a conductance measurement is made with the distal electrodes as described above. This measurement may then be used to determine not only whether a valid titration can be performed at all, but also may be used to correct the titration measurement with respect to the measured conductivity. This can be a significant factor in enhancing measurement accuracy without significantly increasing the complexity of the titration measurement or the time required to perform it.

What is claimed is:

1. A multimode electrochemical sensing array comprising a semiconductor chip having formed thereon:
    A. an Ion Selective Field Effect Transistor, said transistor having an exposed Gate for contact with a test solution when immersed therein, said Gate being surrounded by, but spaced from, a conductive surface that serves as both an electrode and a light shield for the transistor;
    B. a plurality of electrodes spaced remotely from said transistor, at least one of said electrodes being connectable in circuit with said conductive surface and with an external current source to provide a current for electrochemical determination of two or more parameters of said solution.

2. A multimode electrochemical sensing array according to claim 1 in which said current source is polarized to provide a titrant in the vicinity of said Gate.

3. A multimode electrochemical sensing array according to claim 1 in which said current source is polarized to provide a titrant in the vicinity of said at least one remotely spaced electrode.

4. A multimode electrochemical sensing array according to claim 1 in which said remotely spaced electrodes includes comprise a first pair of electrodes, each of a first area, and a second pair of electrodes, each of a smaller area than said first area, said electrodes being connectable in circuit with an external current source and an external voltage meter to provide conductivity measurements of a test solution in which they are immersed.

5. A multimode electrochemical sensing array according to claim 1 in which said remotely spaced electrodes include at least one electrode for performing oxidation/reduction measurements with respect to an external reference electrode.

6. A multimode electrochemical sensing array according to claim 1 in which said remotely spaced electrodes include at least one electrode connectable through a potential regulating element to said conductive surface for limiting the potential on said surface.

7. A multimode electrochemical sensing array according to claim 6 in which said potential regulating element comprises a varistor.

8. A multimode electrochemical sensing array according to claim 1 in which said remotely spaced electrodes include at least one electrode connectable to ground to thereby connect a test solution to ground potential when desired.

9. A multimode electrochemical sensing array according to claim 1 in which said at least one electrode is connectable in circuit with an external source of constant current.

10. A multimode electrochemical sensing array according to claim 1 in which said at least one electrode is connectable in circuit with an external source of current that increases during its application.

11. A multimode electrochemical sensing array according to claim 1 in which said at least one electrode is connectable in circuit with an external source of current that increases linearly during its application over at least some range thereof.

\* \* \* \* \*